(12) United States Patent
Janowiak et al.

(10) Patent No.: US 10,898,599 B2
(45) Date of Patent: Jan. 26, 2021

(54) RADIO FREQUENCY TREATMENT TO PHYTOSANITIZE WOOD PACKAGING MATERIALS USED IN INTERNATIONAL SHIPPING

(71) Applicant: The Penn State Research Foundation, University Park, PA (US)

(72) Inventors: John J. Janowiak, Julian, PA (US); Kelli Hoover, Pennsylvania Furnace, PA (US); Ronald G. Mack, Chatham, MA (US)

(73) Assignees: THE PENN STATE RESEARCH FOUNDATION, University Park, PA (US); UNITED STATES, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 383 days.

(21) Appl. No.: 15/854,121

(22) Filed: Dec. 26, 2017

(65) Prior Publication Data
US 2018/0177904 A1    Jun. 28, 2018

Related U.S. Application Data

(60) Provisional application No. 62/531,206, filed on Jul. 11, 2017, provisional application No. 62/439,314, filed on Dec. 27, 2016.

(51) Int. Cl.
| | |
|---|---|
| *A61L 2/08* | (2006.01) |
| *B27K 5/00* | (2006.01) |
| *H05B 6/62* | (2006.01) |

(52) U.S. Cl.
CPC ............ *A61L 2/08* (2013.01); *B27K 5/001* (2013.01); *B27K 5/0055* (2013.01); *H05B 6/62* (2013.01); *B27K 2240/20* (2013.01)

(58) Field of Classification Search
CPC ......... A61L 2/08; B27K 5/001; B27K 5/0055; H05B 6/62
See application file for complete search history.

(56) References Cited

U.S. PATENT DOCUMENTS

| | | | | |
|---|---|---|---|---|
| 3,031,767 | A * | 5/1962 | Wood | F26B 3/34 34/256 |
| 3,986,268 | A * | 10/1976 | Koppelman | F26B 7/00 34/257 |
| 8,578,625 | B2 | 11/2013 | Franich et al. | |
| 9,440,372 | B2 | 9/2016 | Holm | |
| 2010/0236088 | A1 | 9/2010 | Paice | |
| 2014/0041248 | A1 | 2/2014 | Franich et al. | |

FOREIGN PATENT DOCUMENTS

WO        2016138910 A1    9/2016

* cited by examiner

*Primary Examiner* — Sean E Conley
(74) *Attorney, Agent, or Firm* — Dinsmore & Shohl LLP

(57) ABSTRACT

A method for treating wood packaging materials using Radio Frequency heating includes the steps of heating wood packaging materials using RF heating and applying a pressure before the heating or incrementally applying a pressure during the heating until a temperature of the wood packaging materials reaches at least 60° C. and that temperature is maintained for at least 1 minute.

23 Claims, 7 Drawing Sheets

RADIO FREQUENCY TREATMENT TO PHYTOSANITIZE WOOD PACKAGING MATERIALS USED IN INTERNATIONAL SHIPPING

CROSS REFERENCE

This application claims priority from Provisional Application No. 62/439,314 filed Dec. 27, 2016, and Provisional Application No. 62/531,206 filed Jul. 11, 2017, the entire content of which are incorporated herein by reference.

STATEMENT OF GOVERNMENT SUPPORT

This invention was made with government support under Hatch Act Project No. PEN04518, awarded by the United States Department of Agriculture/NIFA and under Grant No. 2014-51102-22282, awarded by the United States Department of Agriculture. The Government has certain rights in the invention.

FIELD OF THE INVENTION

The present invention relates to the use of radio frequency (RF) for the rapid phytosanitary treatment of commercial-sized loads of wood packaging materials.

BACKGROUND OF THE INVENTION

Wood packaging material (WPM; e.g. pallets, crates, and dunnage) is a vital part of global trade and the forest products industry. Pallets "move the world," with several billion pallets used each day around the globe in domestic and international shipping. An estimated 50-80% of the US $12 trillion in world merchandise trade is moved using some form of WPM and more than 1.8 billion pallets are in service each day, and 93% of these are made from wood. In the U.S., roughly 700 million wooden pallets are produced per year. Untreated WPM is recognized as one of the major pathways by which wood boring insects and plant pathogens move among countries. In 2002, the International Plant Protection Convention (IPPC) established a requirement that all WPM be treated to reduce the risk of spread of quarantine pests. The International Standard of Phytosanitary Measures No. 15 (ISPM-15), adopted in 2014 by the IPPC of the UN after country consultation, mandated that all WPM used in international trade be treated by methyl bromide fumigation or conventional heat treatment to 56° C. at the core of the wood for 30 minutes.

Methyl bromide is classified as a carcinogen and also an ozone depleting gas with implications for global warming, which led to banning of this chemical in many countries. Methyl bromide is being phased out in the US and Europe (under the Montreal Protocol). Wood has inherently high insulation properties due to its cellular composition. Thus, the transfer of sufficient heat through wood to reach lethal temperatures for pests that infest the wood is slow using conventional heating. Conventional heating does not always kill all pests of concern. So the IPPC (International Plant Protection Committee—UN FAO) Secretariat put out a call for new treatments to be developed and submitted for approval to augment current ISPM-15 treatments.

With the addition of dielectric heating, e.g., RF and microwave (MW) to the approved treatments under ISPM-15, the treatment schedule requires that the wood temperature reach and hold 60° C., but the hold time at that temperature is only for 1 minute. Conventional heating under ISPM-15 requires a much longer 30-minute hold period once the WPM reaches a prescribed 56° C. core temperature and requires preheating of the oven.

MW also heats volumetrically by interacting with water molecules in the treated materials, but the frequency is much higher, ranging from 915 MHz to 2.45 GHz for most US commercial units e.g. heating oven applications. However, in direct contrast to MWs, RF dielectric applications use lower frequency irradiation with much longer wavelengths and thus can effectively penetrate materials more deeply allowing phytosanitation treatment of larger sections or volume of workloads of WPM.

SUMMARY OF THE INVENTION

Dielectric heating occurs through two mechanisms: dipole rotation and ionic conduction. For RF, dipole rotation occurs when the material being treated contains polar molecules (positive and negative charges on opposite ends, like the water moisture within the wood), which subsequently align in the electrical field produced by dielectrically charged plates. The field alternates millions of times per second (1 MHz=1 million cycles per second), causing the polar molecules in the treated material to constantly rotate to align with the plates, producing friction that generates heat. Also, charged particles (ions) in the material are heated constantly as they move to the opposite electromagnetic plate charge, adding more friction. These processes generate substantial kinetic energy (heat) that results in the whole volume of the product being heated at once, not just the surface, which is referred to as volumetric heating. As a result, the targeted WPM experiences rapid internal thermal heating in comparison to conventional or conductive heat transfer mechanisms.

RF does not require pre-heating and the chamber does not get hot during operation; most of the energy is directly absorbed by the product being heated rather than having to be transferred from the surface to the core of the product. RF can selectively heat insects over the product due to the higher water content of insects with respect to the product being treated (Nelson, S. O. 1996. Review and assessment of radio-frequency and microwave energy for stored-grain insect control. American Society of Agricultural Engineers 39(4): 1475-1484).

In our experiments using RF to bulk treat raw wood to be used to construct crates and pallets, we found that substantial heating energy losses with a plateau or decline in temperature elevation occurs as the wood approaches or exceeds a critical temperature of approximately 50° C. This is due to water movement or vapor release during evaporative cooling, causing a non-steady heating unless significantly more power density is added in order to reach the required temperature of 60° C. through the profile of the materials being treated (per ISPM-15 schedule requirements). This WPM heating behavior causes both an increased treatment cost and an associated loss in ISPM-15 processing efficiency. Various techniques investigated include use of a thermal insulation barrier to contain heating losses resulting in some heating improvements but are not practical for large volume treatments.

The present invention provides a method in which heating behavior within large batches of WPM can be effectively controlled to reduce energy costs and increase treating capacity by applying a pressurization technique in conjunction with the operational functioning of the RF equipment. It was experimentally observed that adding controlled pressure levels of about 10-15 psi saved several hours of workload treatment time without having to increase the applied power density to satisfy the ISPM-15 treatment schedule.

In an embodiment of our invention, we have added a pressurization system to RF technology to allow WPM to reach the target temperature of the ISPM-15 schedule much faster. This approach works by maintaining a more constant heating rate during treatment and indirectly serves to better control temperature variations within the volumetric workload for purpose of an enhanced treatment quality control measure. In one version, the heating rate may be constant. In another version, a ramped heating rate may be applied. If the heating rate is constant, it is easier to monitor the process in terms of a predicted time to completion to reach a particular treatment time schedule. By minimizing thermal energy disparities within the wood load, greater heating uniformity can be achieved, which also avoids temperature extremes that otherwise can damage or degrade the WPM materials. As a result of the present invention, significant treatment cost savings can be realized by minimizing energy consumption and reducing moisture loss of the WPM, providing overall improvements in the processing efficiency while complying with ISPM-15 standard requirements.

The method may be carried by a RF operating unit, including a sealed chamber having two primary electrodes inside the chamber, i.e., a top electrode and a bottom ground electrode. A RF generator is connected to the electrodes for applying RF heating treatment to the WPM. A pressurization system is connected to the chamber for controlling the pressure inside the chamber. The system may typically include an infeed/outfeed track loader for simplification of loading and unloading the WPM workload, which reduces labor intensity.

The pressure may be applied incrementally during the heating or applied fully before the heating cycle begins.

In some versions, the step of applying pressure to the chamber includes maintaining the chamber generally at a first pressure, such as approximately atmospheric pressure, during a first period and changing the pressure in the chamber generally to a second pressure after the first period. The second pressure may be at least 10 psi above atmospheric, such as approximately 15 psi above atmospheric. The first period may be defined by a passage of time or in terms of temperature of the WPMs. In one example, the first period is a time period that is predetermined based on the WPMs being treated. Alternatively, the first period may be defined as when the WPMs reach a threshold temperature. For example, the first period may end when at least some of the WPMs reach a threshold temperature in the range of 30 to 60 degrees Celsius, such as approximately 50 degrees Celsius.

The temperature of the workload during the heating may be monitored using RF compatible temperature sensors placed within the workload or via an infrared (IR) surface scanning system to implement commercial quality control measures. In some versions, the "temperature of the WPMs" means an average temperature from the sensors or a maximum reading of any of the sensors or a minimum of any of the sensors.

When the pressure is applied incrementally, the applying of the pressure step may include applying 5 psi of pressure before reaching a rise of 10° C. from an initial ambient temperature of the workload and adding another 5-10 psi to the chamber when 50° C. is first registered by a strategic placement of temperature sensors within the batch workload.

It is preferred that the wood not be heated to a temperature where curing occurs in terms of a significant moisture content loss where the WPM may remain near its original untreated condition or green state with moistures equal or near the fiber saturation level. It is preferred that the moisture content, after treatment, does not appreciably alter the characteristics of the WPM, such as mechanical properties (e.g., fastener installation and cant material resawing properties), are not substantially changed.

For this reason, it is preferred that the wood temperature stay below 100° C., and in some embodiments below 90° C., in further embodiments below 80° C., and, as stated above, typically temperatures below 70° C. are used. However, the temperature should nominally reach the prescribed 60° C. threshold to kill any life cycle pest infesting the WPM. It is preferred that the hold time is not longer than 2-5 minutes at or above the prescribed 60° C. temperature elevation.

After reaching at least 60° C. with a 1-minute hold time, the chamber may be depressurized. The depressurizing of the chamber may be done at a constant rate. After the heating treatment and depressurization, the workload may be removed from the chamber for cooling and post-treatment construction of shipping materials.

The surface temperature of the workload may be further checked using surface temperature imaging technology after the depressurization step to further verify that adequate phyosanitation treatment was achieved in compliance with ISPM-15.

Our preliminary experiments using the method of the present invention in RF processing technology showed a reduction in moisture losses within the batch of treated materials to help avoid drying-related wood surface checking defects. We also saw reduced evaporative cooling, which is a process that significantly increases the time (and energy input) required to reach lethal temperatures to kill all pests infesting the wood being treated.

Our research on both MW and RF and interactions with the industry have clearly shown that RF is far more likely to be adopted than MW because of its greater depth of electromagnetic field wave penetration and ability to bulk treat WPM, which is something MW cannot do under normal operational or application circumstances (Dubey et. al. 2016).

Certain embodiments of the present invention may have three very significant benefits: 1) it keeps electrical power consumption to a minimum, thereby reducing operational energy costs; 2) allows for greater processing efficiency, which will increase capacity for the company, producing a higher return on the capital investment in the equipment; and 3) RF is a more environmentally friendly replacement to methyl bromide fumigation and conventional heating, producing lower carbon emissions as the industry seeks to comply with ISPM-15 to reduce risks of movement of pests in WPM used in international shipping (and now domestic shipping as well with new rules).

This technology could be applied to not only effectively treat WPM but it would also benefit RF treating schedules used for other commodities such as phytosanitation of sawn timbers used extensively in timber frame construction, for either domestic or imported products. Also this innovation could be equally applied to round wood sections, such as export wooden sawbolts or sawlogs. This innovation is also applicable to control the desired temperature elevation for phytosanitary workloads involving RF treatment of wood chips (domestic use or for export), where the heat dissipation factor via water evaporative cooling effects is enhanced due to increased wood surface area that permits greater losses of stored thermal energy.

BRIEF DESCRIPTION OF THE DRAWINGS

The accompanying drawings, which are included to provide a further understanding of the invention and are incorporated in and constitute a part of this application, illustrate embodiment s of the invention and together with the description serve to explain the principle of the invention. In the drawings.

DETAILED DESCRIPTION OF THE INVENTION

Figure 1:
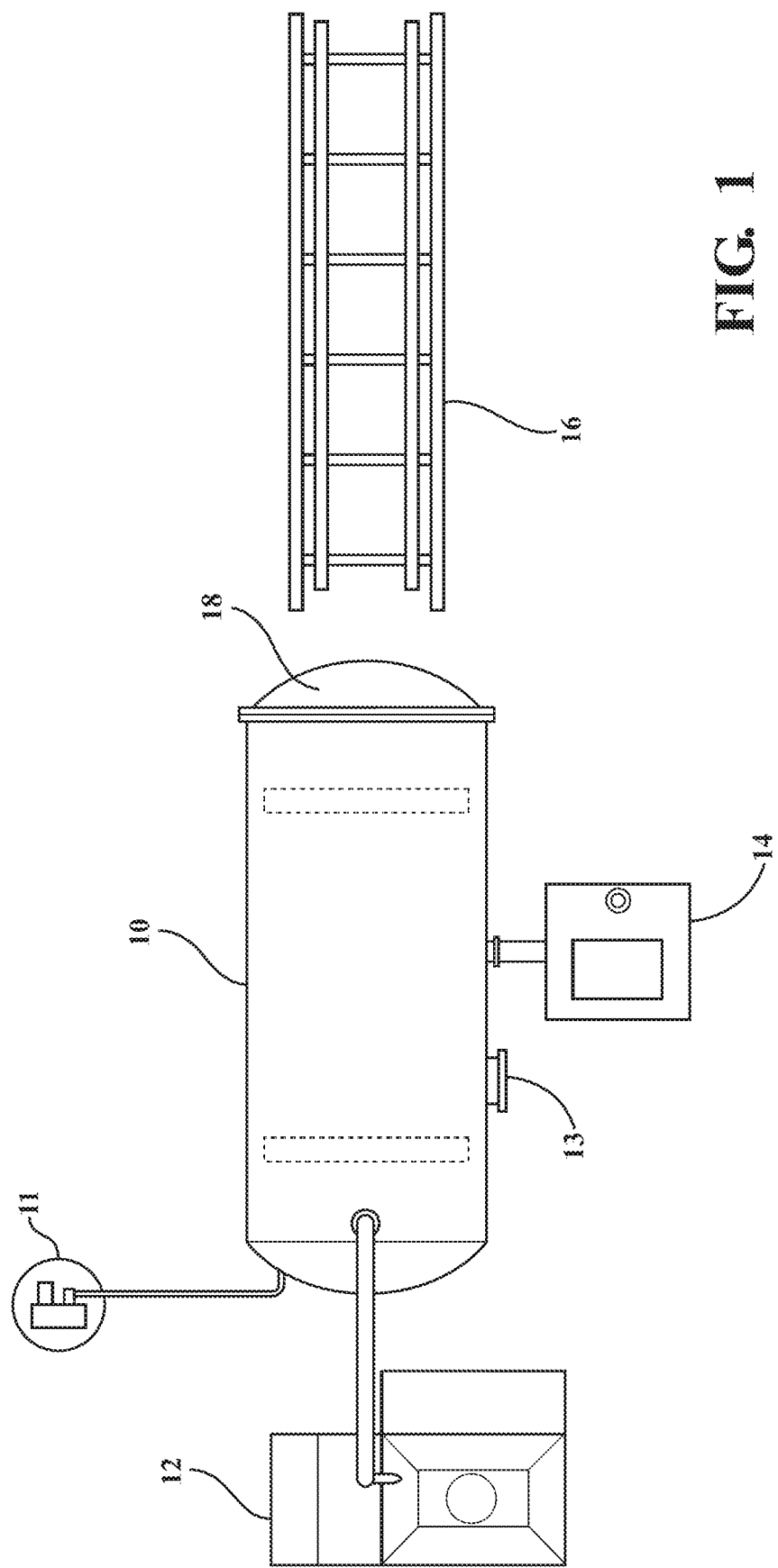
FIG. 1 is a schematic view of an equipment layout for RF equipment in accordance with one embodiment of the present invention.
Figure 2:
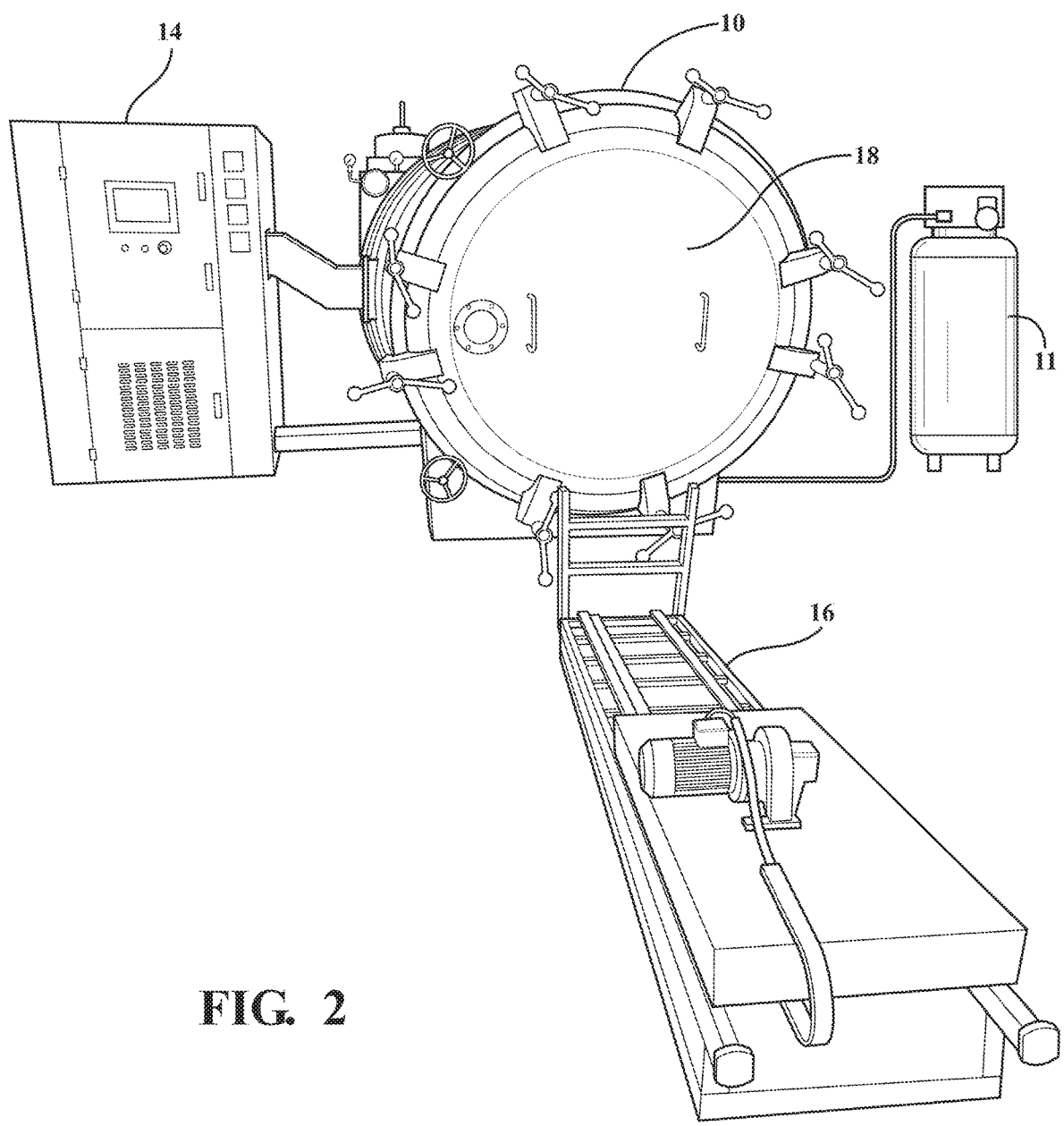
FIG. 2 is a front view of the equipment of FIG. 1 with the chamber door closed.
Figure 3:
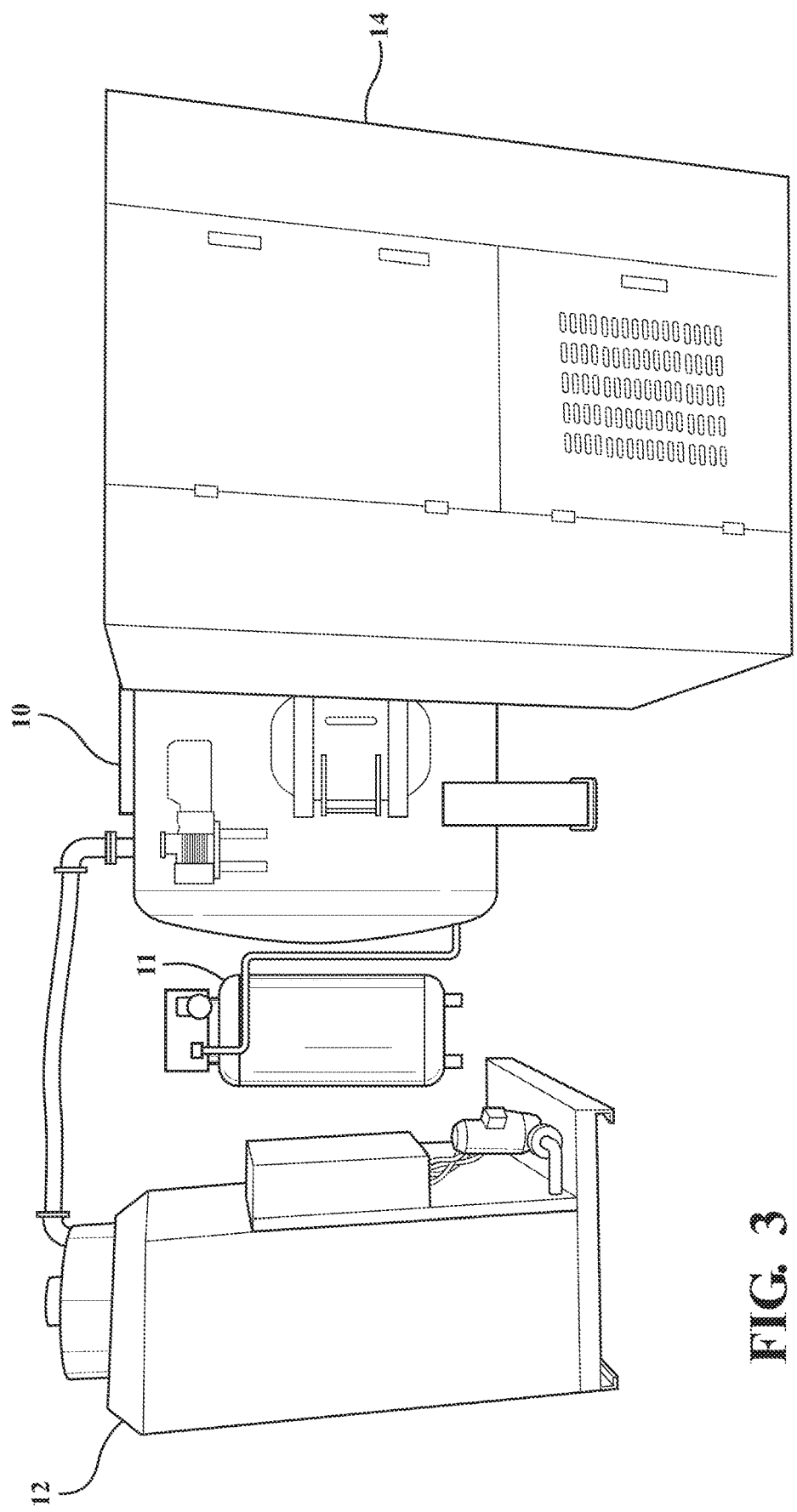
FIG. 3 is a side view of the equipment of FIG. 1.

FIG. 1 is a schematic view of an exemplary layout of a radio frequency system for RF dielectric treatment of the wood packaging materials (WPMs). In one embodiment, as shown in FIG. 1, the system arrangement includes a sealed chamber 10, used as a pressurization treating cylinder or treatment retort, a pressurization system 11, e.g. an air supply pump for retort pressurization, a RF operational cooling system 12, a RF (3-30 MHz) electromagnetic input power generator (oscillator or other) 14, with a suitable integrated PLC control system as the functional mechanism for applied power density to regulate targeted WPM heating rates, and an infeed/outfeed track loader 16 for loading and unloading of the workload. Overall, the cooling system of higher power RF heating units must be suited for rapid cycle sanitization, e.g., those that run with applied operational power below 30-50 kW, which may optionally include only an air-induction fan system for cooling to dissipate excess RF tube heat The chamber 10 shown in the center region of the layout may be an adequate construction cylinder or box-shaped design. In one example, the chamber 10 is the type of chambers used for vacuum with moisture drying treatments of wood, in the form of sawn lumber and timbers. Our design was specifically modified to allow or enable chamber retort pressurization. The chamber 10 can include either a manual or hydraulic sealable door 18 which can be freely swung open or closed to facilitate loading/unloading the volumetric batches of WPM.

Figure 4:
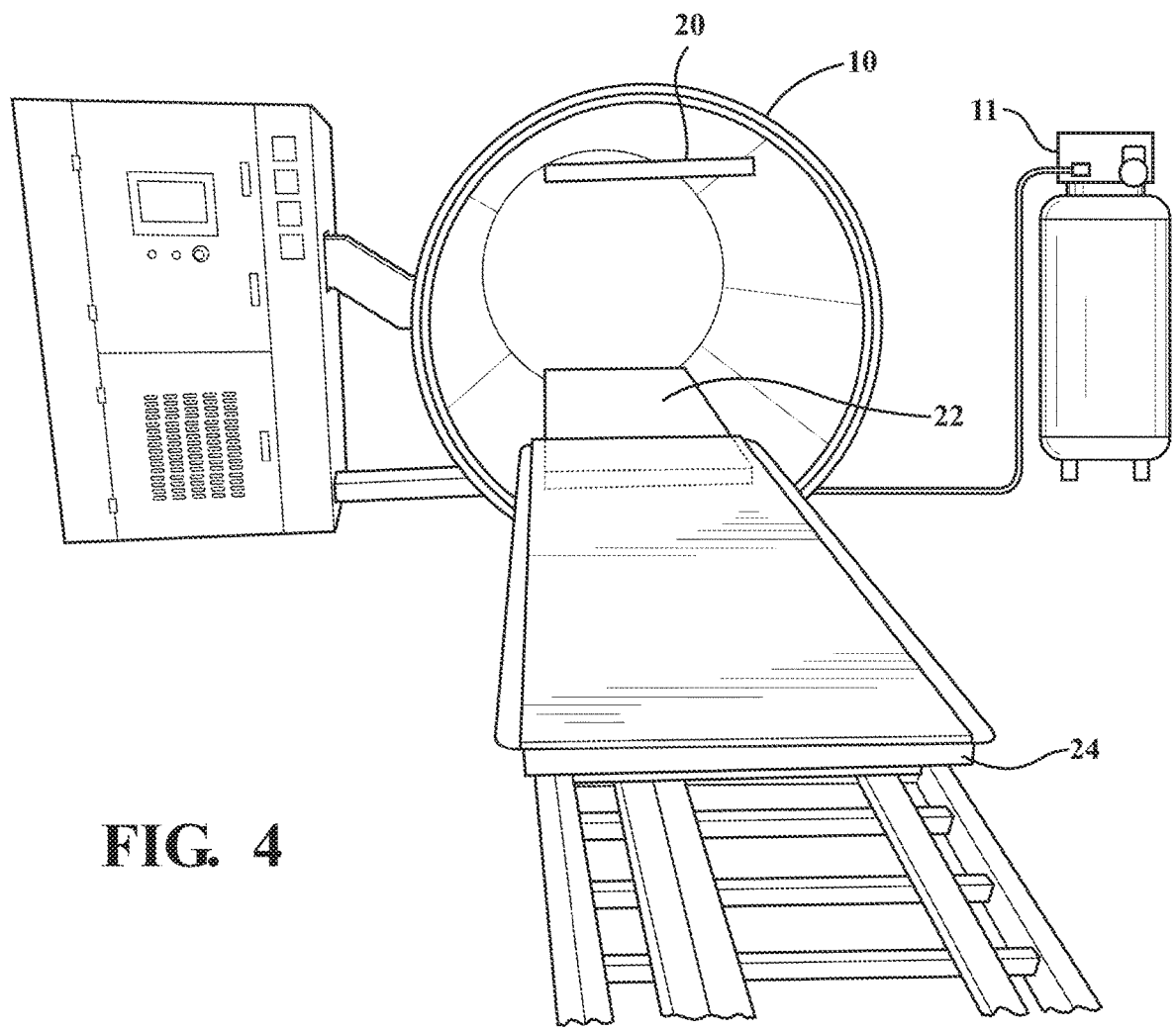
FIG. 4 is a front view of the equipment of FIG. 1 with the chamber door open.

FIG. 4 shows a front view showing inside the chamber. The chamber 10 includes two primary electrodes including a retractable compression electrode plate 20 as the top electrode and a ground electrode 22. The retractable compression top electrode plate 20 is lowered or retracted by air cylinders between the loading and the unloading of the workload. The bottom ground electrode is in a position fixed inside the lower portion of the retort 10. As the workload is fed into the chamber 10 by the infeed/outfeed track as the workload transport loader 16, the volumetric workload is placed on the transport table 24 and positioned between the top electrode 20 and the bottom ground electrode 22. The top electrode applies a download load pressing down onto the workload to assist or remove the air gaps between the top electrode and the lower ground electrode.

Figure 5:
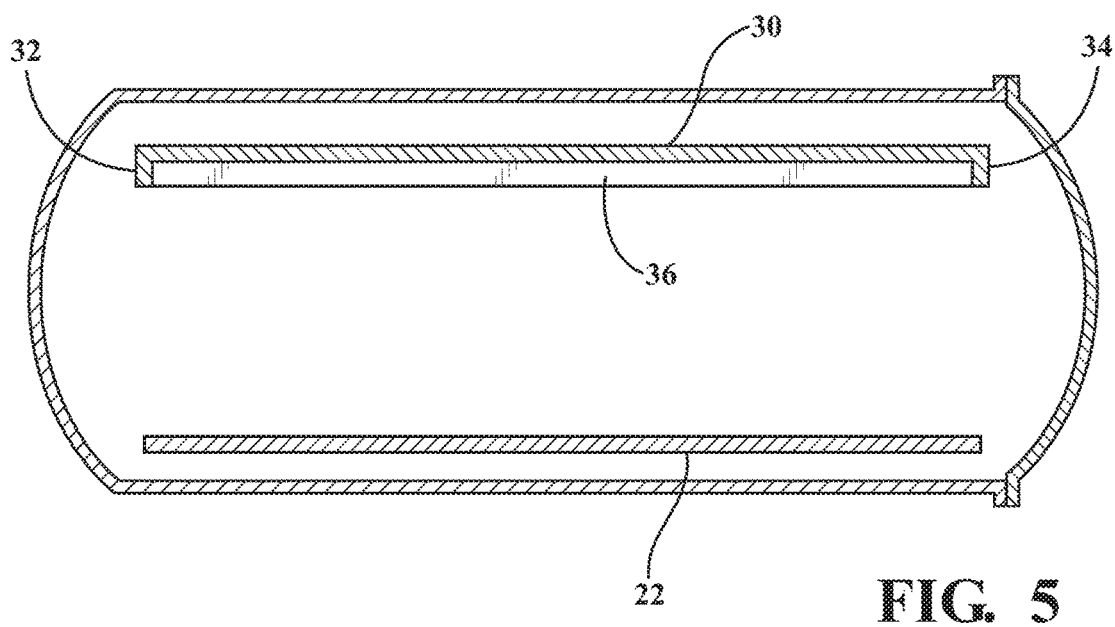
FIG. 5 is a cross-sectional side view of the chamber in accordance with another embodiment of the present invention.

Additional secondary electrodes may be used to improve the energy field distribution depending on the depth of the workload. Secondary electrodes may be statically placed between the built up rows of WPM to be treated and applied as a batch treatment. The secondary electrodes are manually removed after the workload is effectively removed from the cylinder. In an alternative embodiment, instead of secondary electrodes, the top flat electrode may be modified with a winged electrode design arrangement. The top flat electrode 30 may include electrode plate wings, e.g., along the entire perimeter of the flat electrode plate 30, including two ends and two sides. FIG. 5 is a cross-sectional view showing three secondary electrodes 32, 34, 36 attached to the flat electrode plate 30, one at each end and one of the parallel sides of the electrode 30, facing the bottom ground electrode 22.

The primary electrode pair or secondary electrodes are connected to the RF power input generator 14. The RF generator 14 supplies an alternating current to introduce an electromagnetic field. In one embodiment, the RF generator has a constant or variable power output of 50 kW or with greater heating rate capacities. In one embodiment, an operational electromagnetic dielectric frequency may be in the range of 5 and 30 MHz or other wavelength frequency suitable to achieve the desired depth of penetration for wave energy adsorption to obtain heating uniformity during dielectric electromagnetic treatment of an entire WPM volume. The pressurization system 12 provides systematic pressurization of the chamber during the active RF treatment. Just as water evaporates at a higher temperature under an air pressure higher than atmosphere, the pressurization technique of the present invention helps to prevent moisture and significant thermal heat energy losses during the phytosanitary heating cycle by RF treatment to more rapidly and cost effectively comply with ISPM treating requirements.

The temperature within the workload may be monitored throughout the treatment. The temperature monitoring may be done by factory-calibrated fiber-optic or other RF compatible temperature sensors. An access port 13 on one side of the retort enables running (routing) of the required fiber-optic sensors inside the retort and continuous monitoring of the workload heating coupled to an independent data collection system.

Some exemplary dimensions of a system in accordance with the present invention are as follows. In one embodiment, the chamber measures 3-m×1-m×1-m. The volume capacity to be heated as shown is equal to −3 cubic meters, although greater capacity workload designs may be built for large-scale commercial treaters. The electrode plates measure roughly 3-m×1-m. The infeed/outfeed track loader measures 4-m×1-m.

An important component of the RF system innovation includes adequate positive pressure control to raise the boiling point of water or otherwise control the conversion of liquid moisture content to a gaseous water vapor phase that results in net moisture content reduction, while also preventing the critical losses of thermal energy needed to rapidly and with desired uniformity elevate the WPM temperatures throughout the bulk volume of the treated load.

The present invention provides a method of treating WPM to eradicate invasive pest organisms using otherwise a conventional RF oven or vacuum operated kiln type of dielectric dryer technology.

Figure 6:
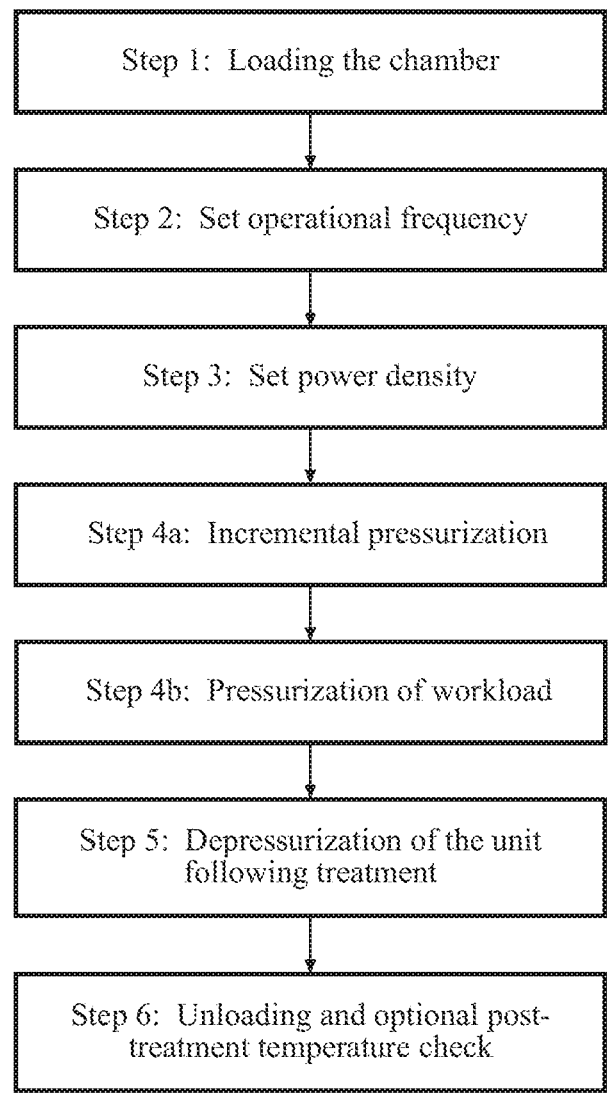
FIG. 6 is a flow chart showing a systematic batch process for pressurization with RF volumetric heat treatment to sanitize WPM in accordance with one embodiment of the present invention

FIG. 6 is a flow chart showing a systematic batch process for pressurization with RF volumetric heat treatment to sanitize WPMs infested with wood pests in compliance with approved ISPM 15 in accordance with one embodiment of the present invention. Each step will be elaborated as follows.

Step 1. Loading the chamber:

Fill the RF operating unit cylinder (Pressure Design Retort) with the WPM Volumetric Load.

The volumetric load may be defined as multiple sawn dimension 4"×6" cants (hardwood/softwood) or other sized raw material pieces to be batch treated prior to conversion into wooden shipping pallets or as otherwise utilized as dunnage for domestic/international commerce.

The unit must be equipped with suitable electrodes to assure compliance with the ISPM-15 treatment schedule for Dielectric Heating (DH), i.e., hold temperature of not less than 60° C. for 1 min through the profile of the workload.

Temperature process monitoring may include factory calibrated fiber-optic or other RF compatible temperature sensors with strategic placement within the workload, consistent with the ISPM-15 standard requirements to monitor heat elevation and uniformity of heating throughout the workload.

Step 2. Set operational frequency:

The next step is to secure the unit retort loading door and apply the appropriate alternating dielectric RF electromagnetic field (EMF). Typical operational frequency is 4 to 50 Hz (EMF oscillations per second).

The appropriate dielectric field will vary as a function of the energy delivered to the targeted workload depth where an ideal frequency is verified based on known or approximated dielectric properties of the WPM, which can vary by wood species and inherent wood moisture content (% MC).

Step 3. Set power density:

Treatment field intensity or application power density vary depending on rated RF generator capacity.

The power density will vary based on the selected RF equipment where higher-power rated designs will increase the processing capacity for a commercial ISPM-15 certified treating facility. Optimum RF heating power relative to pressurization is a function of the combined interactions of material density with weighted % MC, wood species permeability, and ambient thermal state of the volumetric batch of the SWP to be treated.

Power density is calculated based on the desired treatment schedule (treatment time, workload size, wood species and moisture content considerations) to be in compliance with ISPM-15. Anticipated operational power density is 2-4 $kW/m^3$.

Step 4a. Incremental Pressurization:

The step of incremental pressurization includes a) applying 5 psi of pressure before reaching a rise of 10° C. from the initial ambient temperature of the workload and b) adding another 5-10 psi to the chamber when 50° C. is first registered by a temperature sensor within the workload.

From experimental results conducted on ash (*Fraxinus* spp.) cants (green SWP measured at or above the fiber saturation point, e.g. >30% wood moisture content), the combination of applied power density (maximum 3.3 $kW/m^3$) and 10 psi pressurization was shown to substantially reduce the total batch treatment time to fully comply with ISPM-15 requirements (60° C. with 1-minute temperature hold), while reducing the required energy consumption, thereby achieving significant operational cost savings.

Step 4b. Pressurization of workload:

Typical starting pressure recommended is in the range of 10-20 lbs per square inch (psi). Higher pressure can be considered as an option to achieve further batch heating uniformity based on observed departure from a constant workload heating rate to minimize treatment duration.

An alternative approach to incremental pressurization may be used where full pressurization is applied before initiating the RF heating cycle.

Step 5. Depressurization of the unit following treatment:

Depressurization should be controlled for a slow release of pressure. Pressure reduction should be applied only after reaching 60° C. with a 1-minute hold time as required by ISPM-15. A rate of decreased pressure of 2-4 psi per post treatment minute is recommended.

Step 6. Unloading and optional post-treatment temperature check:

An optional step following decompression is to check surface workload temperatures using surface temperature imaging technology, such as IR. Then open the unit door and remove the workload to verify ISPM-15 compliance. The workload is removed for cooling and post-treatment construction of shipping materials.

During this RF treating process, RF heating is applied to the WPMs while a pressure is added to the chamber, until the WPMs are heated to a temperature of about 60° C., but preferably less than 90° C., for a hold time from 60 sec to a few minutes. Under this operating condition, the moisture inside the WPMs is mostly preserved. It is preferred that the wood not be heated to a temperature where curing occurs in terms of a significant moisture content loss where the WPM may remain near its original untreated condition or green state with moistures equal or near the fiber saturation level. For this reason, it is preferred that the wood temperature stay below 100° C., and in some embodiments below 90° C., in further embodiments below 80° C., and, as stated above, typically temperatures below 70° C. are used. However, the temperature should nominally reach the prescribed 60° C. threshold to kill any life cycle pest infesting the WPM. Pressures in the range of 10-20 psi are preferred, with 15 psi being typical. It is preferred that the hold time is not longer than 5 minutes at or above 60° C., in some embodiments not longer than 4 minutes, and in further embodiments not longer than 3 minutes, and in still further embodiments not longer than 2 minutes. As noted above, it is preferred that the moisture inside the wood is mostly maintained for ease of post-treatment conversion to wooden constructed shipping pallets or other packaging end-use applications. In some embodiments, this means that the moisture content, after treatment, remains in the original range of wood fiber saturation typically 28 to 30% MC and in further embodiments it means that the moisture content is not reduced by more than a few percentage of the original wood moisture content. For some embodiments, it is preferred that the moisture content of the wood averages (some pieces may be drier and some may be wetter) at least approximately 28% before the process starts.

In an alternative process, the step of applying pressure to the chamber includes maintaining the chamber generally at a first pressure, such as approximately atmospheric pressure, during a first period and changing the pressure in the chamber generally to a second pressure after the first period. The second pressure may be at least 10 psi above atmospheric, such as approximately 15 psi above atmospheric. The first period may be defined by a passage of time or in terms of temperature of the WPMs. In one example, the first period is a time period that is predetermined based on the WPMs being treated. Alternatively, the first period may be defined as when the WPMs reach a threshold temperature. For example, the first period may end when at least some of the WPMs reach a threshold temperature in the range of 30 to 60 degrees Celsius, such as approximately 50 degrees Celsius. The temperature of the WPMs may be an average temperature from the sensors or a maximum reading of any of the sensors or a minimum of any of the sensors.

It may be preferred to not apply pressure until after a period of time or until a temperature increase is made. This allows moisture from an inner part of a load of WPMs to migrate to the surface, thereby allowing more even heating of the load of WPMs. It may also be preferred that the load of WPMs is arranged such that air gaps are reduced, and a load may be applied vertically and/or horizontally to reduce the air gaps. In one example, the WPMs are randomized or rearranged such that portions that were outside in a bundle are now inside and vice versa. The wood pieces may also be cut from the as-received size prior to treatment and then re-stacked. The use of thinner or smaller wood pieces allows for reduced air gaps since the thinner or smaller pieces will deform under a load during treatment more easily than larger pieces. According to an alternative embodiment, wood chips may be treated and be considered as the WPM.

Figure 7:
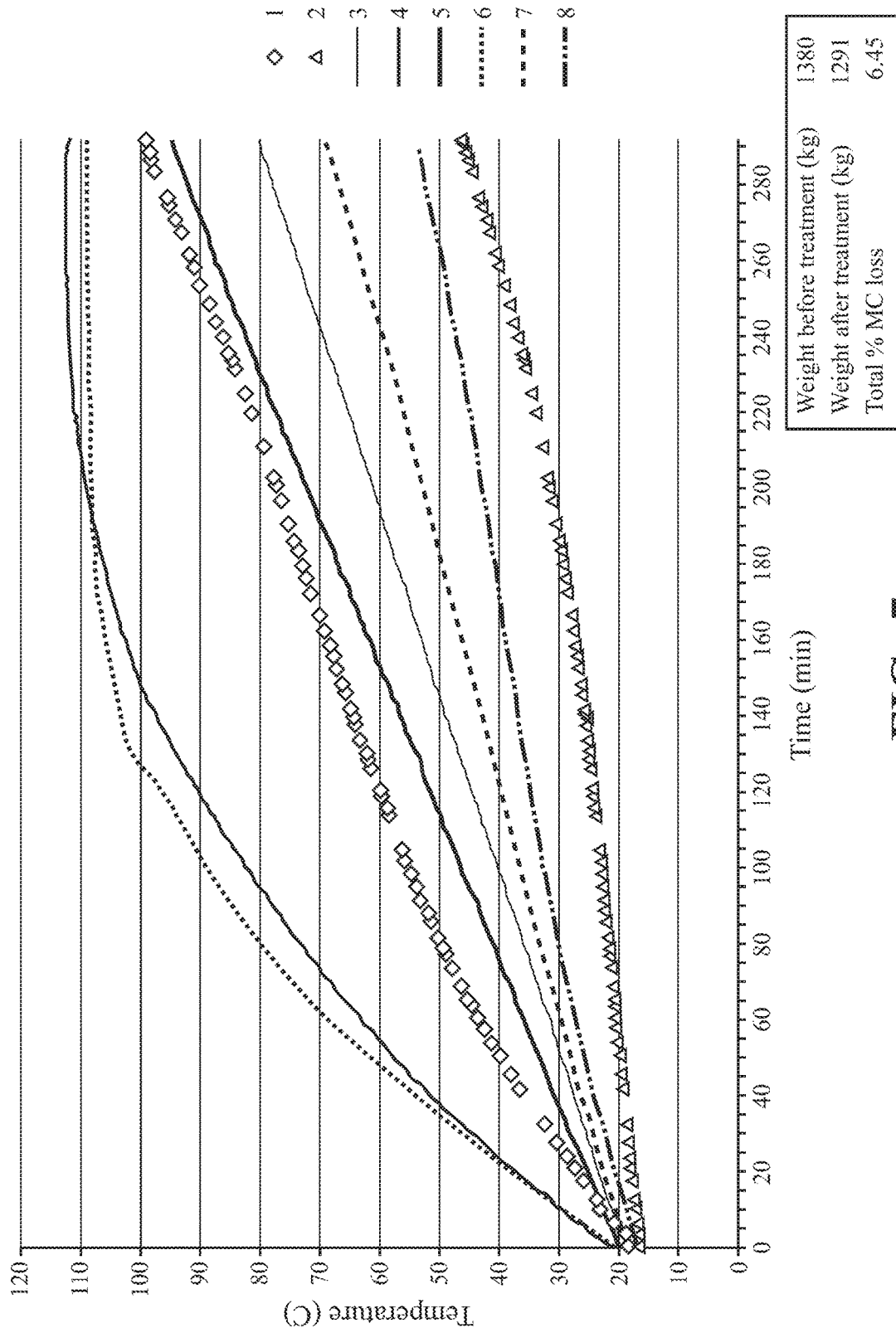
FIG. 7 is a graph showing the temperature rise in wood samples being treated without the application of pressure.
Figure 8:
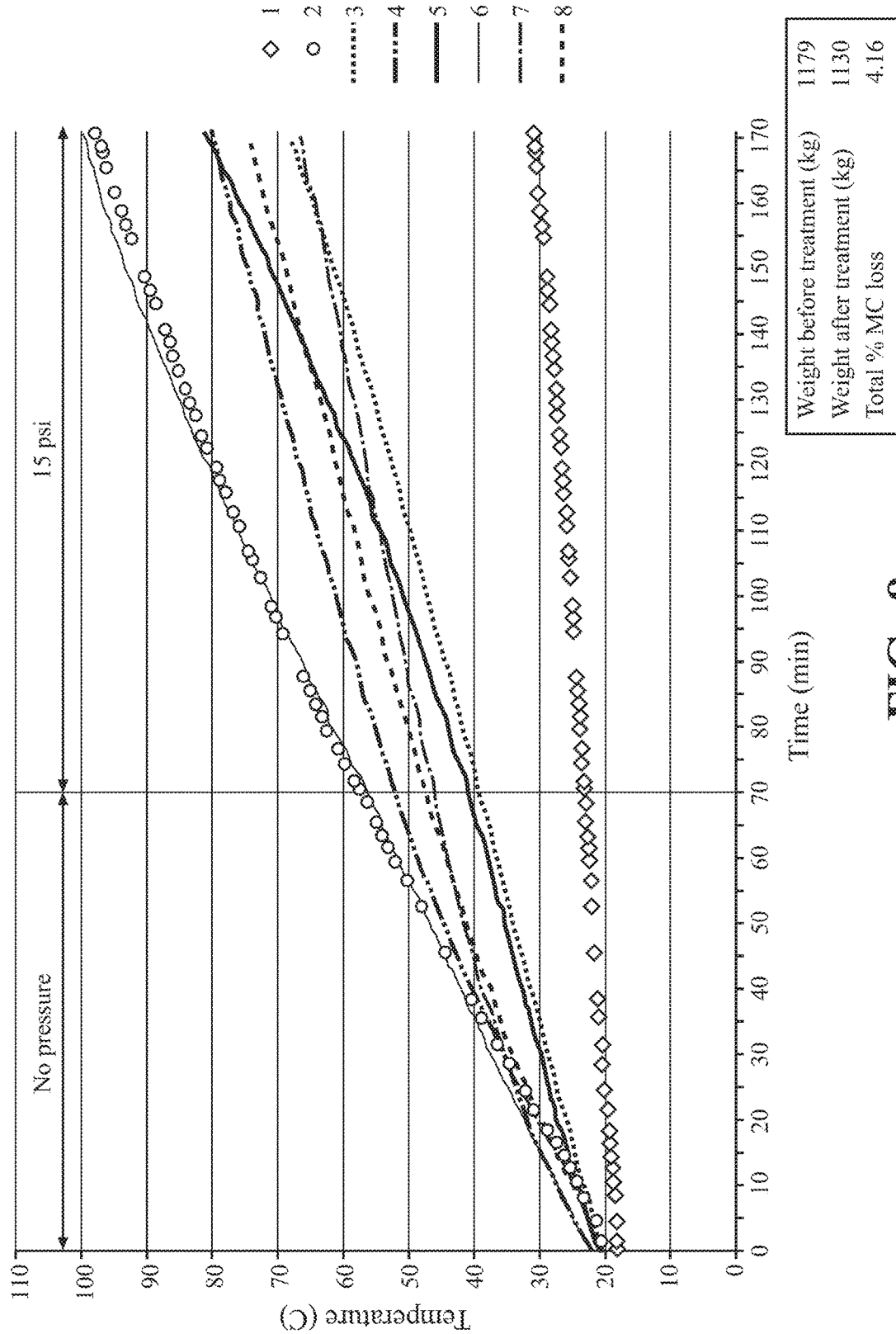
FIG. 8 is a graph showing the temperature rise in wood samples being treated with the application of pressure after a period of time has elapsed.

FIGS. 7 and 8 include experimental data demonstrating certain aspects of an embodiment of the present invention. FIG. 7 is a graph showing the temperature rise in wood samples being treated without the application of pressure. As shown, some portions of the load heat very quickly and reach a temperature of 100 degrees Celsius while other portions of the load heat very slowly. In this test, it is believed that the lowest temperature reading may be an error. However, even if this data is ignored, it still took approximately 280 minutes for most of the load to reach 60 degrees Celcius. As noted, the moisture content dropped by 6.45 percent. FIG. 8 is a graph showing the temperature rise in wood samples being treated with the application of pressure after a period of time has elapsed. Specifically, the chamber was maintained at approximately atmospheric pressure for approximately 70 minutes. The term "approximately atmospheric pressure" is used herein to indicate that additional pressure is not applied. However, some pressure increase may occur due to the heating of the chamber. As with FIG. 7, it is believed that the lowest temperature reading in FIG. 8 is an error. At the point where at least some of the WPMs reach a threshold temperature of 50 degrees Celcius, the pressure is increased to approximately 15 psi above atmospheric. As shown, the temperature readings in the chamber remaining closely grouped and all readings (save for the erroneous lowest reading) reach a treatment temperature of 60 degrees Celcius after approximately 150 minutes, at which point no readings are at 100 degrees Celcius. The treatment time is dramatically reduced, and the moisture content loss is only 4.16 percent.

In one embodiment, the system has a 3-phase electrical source of 480 or optional 600 volts and a total input power of 125-150 amps at 480 volts, supplied by the service alternating current (voltage with power input) transformer.

In one embodiment, the system includes a cooling system having a cooling capacity of 159960 kcal/h or higher. The cooling system may be an evaporative cooling system comprised of stainless steel cabinets, heat exchangers, water circulation pumps and exhaust fans.

In one version, the system includes a fully-automated control system having touch screen controls. The control system is operable to perform temperature monitoring and control, moisture content monitoring and control, cooling system monitoring and control, and pressure monitoring and control.

In one version, when fully assembled and before the infeed cart is fed into the chamber, the footprint of the equipment is about 12 m L×4.3 m W×2.63 m H.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

What is claimed is:

1. A method of treating wood packaging materials (WPMs) using Radio Frequency heating, the method comprising the steps of:
   providing a RF operating unit including:
   a sealed chamber,
   a RF generator connected to the chamber for applying RF heating treatment to the WPMs,
   a pressurization system for controlling the pressure inside the chamber;
   loading the chamber with a workload of the WPMs;
   applying a pressure to the chamber during the treatment, the pressure being at least 5 psi above atmospheric pressure;
   treating the WPMs using RF heating until a temperature of the WPMs reaches a predetermined temperature not more than 100° C.; and
   maintaining the predetermined temperature for at least 1 minute.

2. The method of treating wood packaging materials in accordance with claim 1, wherein the temperature of the WPMs is an average temperature of the WPMs.

3. The method of treating wood packaging materials in accordance with claim 1, wherein the predetermined temperature is not less than 60° C.

4. The method of treating wood packaging materials in accordance with claim 1, wherein the predetermined temperature is not more than a maximum temperature of 90° C., 80° C. or 70° C.

5. A method of treating wood packaging materials (WPMs) using Radio Frequency heating, the method comprising the steps of:
   providing a RF operating unit including:
   a sealed chamber,
   a RF generator connected to the chamber for applying RF heating treatment to the WPMs,
   a pressurization system for controlling the pressure inside the chamber;
   loading the chamber with a workload of the WPMs;
   applying a pressure to the chamber during the treatment;
   treating the WPMs using RF heating until a temperature of the WPMs reaches a predetermined temperature not more than 100° C.; and
   maintaining the predetermined temperature for at least 1 minute, but not longer than a period of 5 minutes, 4 minutes, 3 minutes or 2 minutes.

6. The method of treating wood packaging materials in accordance with claim 1, wherein the step of applying of the pressure to the chamber comprises maintaining the chamber generally at a first pressure during a first period and changing the pressure in the chamber generally to a second pressure after the first period.

7. The method of treating wood packaging materials in accordance with claim 6, wherein the first pressure is approximately atmospheric pressure and the second pressure is greater than atmospheric pressure.

8. The method of treating wood packaging materials in accordance with claim 7, wherein the second pressure is at least 10 psi above atmospheric pressure.

9. The method of treating wood packaging materials in accordance with claim 7, wherein the first period is defined by elapsed time, the elapsed time period being predefined based on the WPMs being treated.

10. The method of treating wood packaging materials in accordance with claim 7, wherein the first period is defined by a temperature threshold, the first period ending when the temperature of at least some of the WPMs reach a temperature threshold in the range of approximately 30° C. to approximately 60° C.

11. The method of treating wood packaging materials in accordance with claim 7, wherein the first period is defined by a temperature threshold, the first period ending when the temperature of at least some of the WPMs reach a temperature threshold of approximately 50° C.

12. The method of treating wood packaging materials in accordance with claim 1, wherein the step of applying pressure to the chamber comprises:
   applying 5 psi of pressure before reaching a rise of 10° C. from an initial ambient temperature of the WPMs; and
   adding another 5-10 psi to the chamber when 50° C. is first registered by a temperature sensor within the WPMs.

13. The method of treating wood packaging materials in accordance with claim 1, further comprising monitoring the temperature of the WPMs using RF compatible temperature sensors placed within the WPMs, the temperature of the WPMs comprises an average temperature from the temperature sensors, a maximum temperature from one of the sensors, or a minimum temperature from one of the sensors.

14. The method of treating wood packaging materials in accordance with claim 1, further comprising depressurizing the chamber after reaching at least 60° C. with a 1-minute hold time.

15. The method of treating wood packaging materials in accordance with claim 14, wherein the depressurizing of the chamber is at a rate of decreased pressure of 2-4 psi per minute.

16. The method of treating wood packaging materials in accordance with claim 15, further comprising checking a surface temperature of the WPMs using surface temperature imaging technology after the depressurization step.

17. The method of treating wood packaging materials in accordance with claim 1, further comprising unloading the WPMs from the chamber for cooling and post-treatment construction of shipping materials.

18. The method of treating wood packaging materials in accordance with claim 1, wherein the RF operating unit further includes two primary electrodes inside the chamber and the RF generator is connected to the primary electrodes, the primary electrodes being a top electrode and a lower ground electrode.

19. The method of treating wood packaging materials in accordance with claim 18, wherein the WPMs are disposed between the two primary electrodes and the top electrode applies a load pressing down onto the WPMs to remove air gaps between the two primary electrodes.

20. The method of treating wood packaging materials in accordance with claim 18, wherein the RF operating unit further includes secondary electrodes.

21. The method of treating wood packaging materials in accordance with claim 18, wherein the primary electrodes include a top winged electrode.

22. The method of treating wood packaging materials in accordance with claim 1, wherein the treating the WPMs using RF heating is at a constant rate or at a ramping rate.

23. The method of treating wood packaging materials in accordance with claim 1, further comprising applying a load to the WPMs to reduce air gaps.

* * * * *